(12) United States Patent
Harder et al.

(10) Patent No.: US 8,528,777 B2
(45) Date of Patent: Sep. 10, 2013

(54) TUBE FOR DNA REACTIONS

(75) Inventors: Chris Harder, Ottawa (CA); Martin Cloake, Ottawa (CA); Michel Perreault, Ottawa (CA); Paul Lem, Ottawa (CA); Alan Shayanpour, Stittsville (CA)

(73) Assignee: Spartan Bioscience Inc., Ottawa, Ontario (CA)

( * ) Notice: Subject to any disclaimer, the term of this patent is extended or adjusted under 35 U.S.C. 154(b) by 605 days.

(21) Appl. No.: 12/753,885

(22) Filed: Apr. 4, 2010

(65) Prior Publication Data

US 2010/0264155 A1 Oct. 21, 2010

(30) Foreign Application Priority Data

Apr. 15, 2009 (CA) ........................... 2662546

(51) Int. Cl.
*B65D 43/08* (2006.01)

(52) U.S. Cl.
USPC .......... 220/796; 220/800; 220/DIG. 19; 220/307; 215/296; 215/355; 215/DIG. 3; 215/DIG. 4; 138/89; 138/90; 422/568

(58) Field of Classification Search
USPC .......... 220/796, 800, 801, DIG. 19; 215/355, 215/DIG. 4, 296, DIG. 3; 138/89–90; 422/568
See application file for complete search history.

(56) References Cited

U.S. PATENT DOCUMENTS

| | | | |
|---|---|---|---|
| 2,801,017 A * | 7/1957 | Cortat | 215/296 |
| 3,017,050 A * | 1/1962 | Barr, Sr. et al. | 215/247 |
| 3,725,010 A | 4/1973 | Penhasi | |
| 3,842,514 A * | 10/1974 | Scheyer | 215/355 |
| 3,898,046 A * | 8/1975 | Ikeda | 215/355 |
| 3,948,261 A * | 4/1976 | Steiner | 604/46 |
| 4,254,082 A * | 3/1981 | Schick et al. | 422/401 |
| 4,257,886 A * | 3/1981 | Kessler | 210/516 |
| 4,531,651 A * | 7/1985 | Donnelly | 215/354 |
| 4,640,434 A * | 2/1987 | Johnsen et al. | 220/287 |
| D289,796 S * | 5/1987 | Larkin | D24/224 |
| 4,755,356 A * | 7/1988 | Robbins et al. | 215/306 |
| 4,841,818 A * | 6/1989 | Plapp et al. | 81/3.08 |
| 4,940,135 A * | 7/1990 | Hall | 206/3 |
| 5,167,929 A * | 12/1992 | Korf et al. | 422/534 |
| 5,325,977 A * | 7/1994 | Haynes et al. | 215/307 |
| 5,484,734 A * | 1/1996 | Kimura | 436/176 |
| 5,552,325 A * | 9/1996 | Nochumson et al. | 422/527 |
| 5,552,580 A | 9/1996 | Pfost et al. | |
| 5,620,662 A * | 4/1997 | Perlman | 215/355 |
| 5,753,186 A * | 5/1998 | Hanley et al. | 422/550 |
| 5,785,925 A * | 7/1998 | U'Ren | 422/72 |
| 6,073,327 A * | 6/2000 | Inoue et al. | 29/235 |
| 6,730,883 B2 | 5/2004 | Brown et al. | |
| 6,878,905 B2 | 4/2005 | Brown et al. | |
| 7,081,600 B2 | 7/2006 | Brown et al. | |
| 2002/0130100 A1* | 9/2002 | Smith | 215/247 |
| 2008/0116204 A1* | 5/2008 | Ohse | 220/254.6 |
| 2008/0287585 A1* | 11/2008 | Brown | 524/424 |

\* cited by examiner

*Primary Examiner* — Mickey Yu
*Assistant Examiner* — Brijesh V. Patel
(74) *Attorney, Agent, or Firm* — Brenda Herschbach Jarrell; Charles E. Lyon; Choate, Hall & Stewart LLP

(57) ABSTRACT

A reaction tube for use in performing the Polymerase Chain Reaction (PCR) in a thermal cycler, is provided herein such reaction tube includes a hollow tube of heat conducting synthetic plastics material having an open top and a flat bottom formed of an optically-clear material. Such reaction tube also includes a solid plug cap nesting within said hollow tube and to provide a minimized void volume within the hollow tube and to minimize evaporation and condensation of the biological fluid.

12 Claims, 1 Drawing Sheet

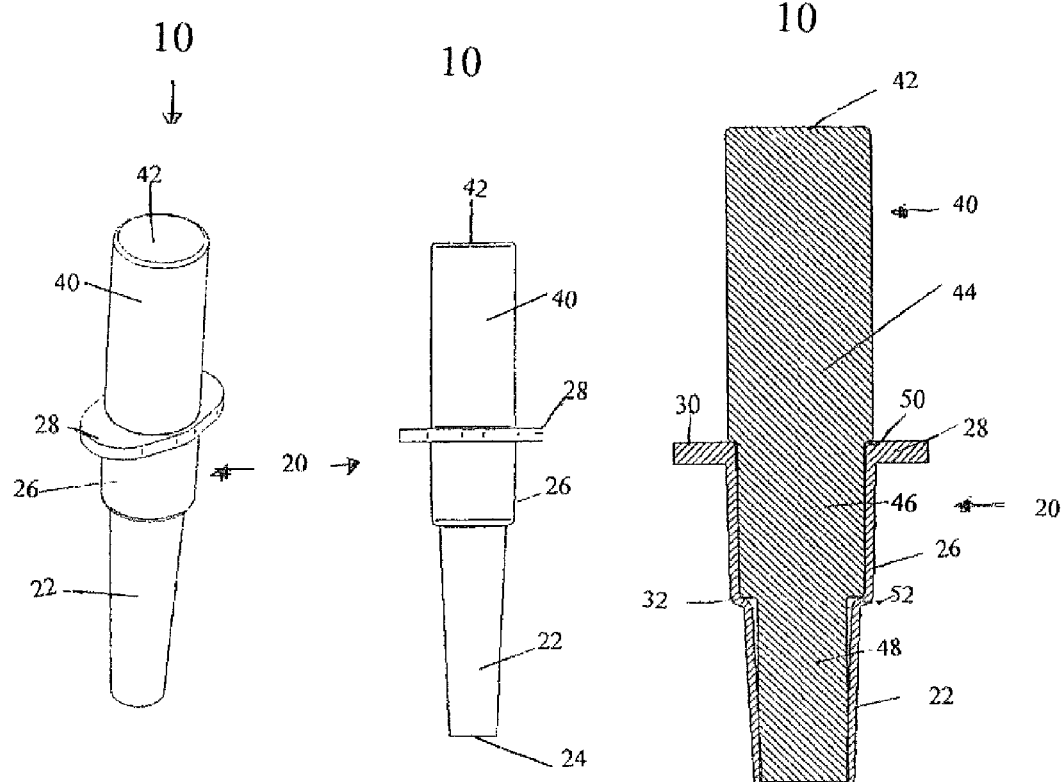

TUBE FOR DNA REACTIONS

BACKGROUND OF THE INVENTION

1. Field of the Invention

This invention relates to reaction tubes which are used in performing the Polymerase Chain Reaction (PCR) in thermal cyclers utilizing temperature controlled heat blocks for heating and cooling.

2. Description of the Prior Art

Thin-walled 0.2 ml polypropylene reaction tubes are the standard for performing the Polymerase Chain Reaction (PCR) in thermal cyclers utilizing temperature-controlled heat blocks for heating and cooling, as disclosed, for example, in U.S. Pat. No. 3,725,010 patented Apr. 3, 1973 by Beckman Instruments Inc. Typically, the reaction tube is inserted into a well in the heat block so that the sides are surrounded by the heat block but the cap is not in contact with the heat block. Since the cap is not in contact with the heat block, it is cooler than the sides of the tube. There are a number of solutions that have been invented to minimize evaporation and condensation of liquid reagents into the cap during the heating and cooling cycles of PCR.

These patented solutions include:

U.S. Pat. No. 7,081,600, patented Jul. 25, 2006 by Stratagene California for "Method and Apparatus for Cover Assembly for Thermal Cycling of Samples". That patent provided a cover assembly for heating a plurality of samples which included a plurality of heater element areas located within a housing, and a force distribution system that engaged the plurality of heater element areas and distributed a force over the plurality of heater element areas, so that the cover assembly flexibly engaged the plurality of samples and heated the plurality of samples. The arrangement of the resistive heater, the heater backing plate, the force distribution system and the support plate allegedly provided substantial temperature uniformity among a plurality of sample tubes for receiving samples of biological material. The flexible heating cover assembly was alleged to improve the uniformity, efficiency, quality, reliability and controllability of the thermal response during thermal cycling of the biological material.

U.S. Pat. No. 6,878,905, patented Apr. 12, 2005 by Stratagene California for "Apparatus and Method For Flexible Heating Cover Assembly For Thermal Cycling of Samples of Biological Material". The patent provided a flexible heating cover assembly for an apparatus for thermal cycling of samples of biological material which included: a housing including a plurality of assembly skirt components; a resistive heater located within the housing, the resistive heater including at least one outer heater element area and at least one central heater element area; a heater backing plate connected to the resistive heater to protect the resistive heater; a load sharing system engaging the heater backing plate to promote uniform contact of the resistive heater with a plurality of sample tubes; and a support plate aligning the assembly skirt components, so that the flexible heating cover assembly provides non-uniform heat distribution among the samples of biological material. The flexible heating cover assembly was alleged to improve the uniformity, efficiency, quality, reliability and controllability of the thermal response during thermal cycling of the biological material.

U.S. Pat. No. 6,730,883, patented May 4, 2004 by Stratagene California for "Flexible Heating Cover Assembly for Thermal Cycling of Samples of Biological Material". The patent provided a flexible heating cover assembly which included a plurality of engageable enclosure components; a resistive heater located within the housing, the resistive heater including a plurality of heater element areas; a heater backing plate engaging the resistive heater and providing stability to the resistive heater; a force distribution system that engaged the heater backing plate and distributed a force over the heater backing plate; and a support plate providing stiffness for the force distribution system, so that the arrangement of the resistive heater, the heater backing plate, the force distribution system and the support plate provide substantial temperature uniformity among a plurality of sample tubes for receiving samples of biological material. The arrangement of the resistive heater, the heater backing plate, the force distribution system and the support plate was alleged to provide substantial temperature uniformity among a plurality of sample tubes for receiving samples of biological material. The flexible heating cover assembly was alleged to improve the uniformity, efficiency, quality, reliability and controllability of the thermal response during thermal cycling of the biological material.

U.S. Pat. No. 5,552,580, patented Sep. 3, 1996 by Beckman Instruments Limited for "Heated Cover Device" provided a heated cover for a receptacle containing a vaporizable substance. The cover was heated to a temperature above the temperature of the substance so as to prevent condensation of vapor evaporated from the substance. A device for placing and removing the cover with respect to the receptacle is designed in connection with a temperature-controlled heating/cooling plate which controls the temperature of the contents of the receptacle. Thus, the heated lid heated the cap to a temperature equivalent or hotter than the sides of the These attempted solutions were not completely effective since, by definition, the use of a heated lid required extra electronics and components compared to a system without a heated lid.

Another proposed solution was to overlay mineral oil atop of the liquid reagents to prevent evaporation at the reaction temperature.

This attempted solution was not completely effective since mineral oil represents an extra reagent that must be added in an extra step. Both of these solutions complicate the process of PCR.

In addition, real-time thermal cyclers combine a thermal cycling apparatus with a system for optical detection of fluorescence generated by a successful PCR. Some Instruments excite and image the reaction through the top of the tube. For example, this is the setup of the "Stepfme" system from Applied Biosystems. That procedure required that the top of the tube be flat and be optically clear.

Other systems excite the reaction from the side and image the reaction from the bottom of the tube. For example, this is the setup of the Spartan DX™ system from Spartan Bioscience. A problem using such system occurs because standard PCR tubes have curved bottoms. The curvature reflects and refracts both the excitation and emission light. This results in light artifacts that reduce sensitivity and specificity of the optical detection.

SUMMARY OF THE INVENTION

Aims of the Invention

An object of one aspect of the present Invention is to minimize evaporation of the biological fluid being subjected to the PCR reaction.

Another object of one aspect of the present invention is to improve optical detection of the biological fluid being subjected to the PCR reaction.

The invention in its general form will first be described, and then its implementation terms of specific embodiments will be detailed with reference to the drawings following hereafter. These embodiments are intended to demonstrate the principle of the invention, and the manner of its implementation. The invention in its broadest sense and more specific forms will then be further described, and defined, in each of the individual claims which conclude this Specification.

STATEMENT OF INVENTION

In general terms, these objects are met by a novel PCR tube that has a plug style cap and a flat, optically-clear bottom. The plug style cap minimizes condensation in two ways. Firstly, the cap descends into the tube and minimizes the void volume. Secondly, because of this structure, heat is transferred from the sides of the tube to the cap. This minimizes the temperature differential between the tube and the cap, and minimizes evaporation and condensation. The flat, optically-clear bottom minimizes reflections and refractions of the excitation and emission light, and improves the sensitivity and specificity of the optical system.

Thus, a broad aspect of the invention provides a reaction tube for use in performing the Polymerase Chain Reaction (PCR) in a thermal cycler, comprising a hollow tube of heat conducting synthetic plastics material having an open top and a flat bottom formed of an optically-clear material, and a solid plug cap nesting within the hollow tube to provide a minimized void volume within the hollow frustoconical tube and to minimizes evaporation and condensation of the biological fluid.

Thus, a broad aspect of the invention provides a reaction tube for use in performing the Polymerase Chain Reaction (PCR) in a thermal cycler, comprising a hollow tube of heat conducting synthetic plastics material having an open top and a flat bottom formed of an optically-clear material, and a solid plug cap nesting within the hollow tube to provide a minimized void volume within the hollow frustoconical tube and to minimizes evaporation and condensation of the biological fluid.

OTHER FEATURES OF THE INVENTION

By one variant of this broad aspect of the invention, the hollow tube includes an upper cylindrical portion.

By another variant of this broad aspect of the invention, the hollow tube includes a lower frustoconical portion.

By another variant of this broad aspect of the invention, the solid plug cap sealingly nests partially within the upper cylindrical portion of the hollow tube and partially within the lower frustoconical portion of the hollow tube.

By another variant of this broad aspect of the invention, the hollow tube includes an upper lip at the upper cylindrical portion of the hollow tube. By a variation thereof, the upper lip is oval in plain view.

By another variant of this broad aspect of the invention, the solid plug cap includes an upper cylindrical portion of greater diameter than the mid-portion thereof, and such upper cylindrical portion of greater diameter than the mid-portion rests upon the upper lip of the upper cylindrical portion of the hollow tube. By another variant of this broad aspect of the invention, the mid-portion of the solid plug cap nests within the upper cylindrical portion of the hollow tube.

By another variant of this broad aspect of the invention, the frustoconical portion of the hollow tube has a draft angle of about 5 degrees.

The foregoing summarizes the principal features of the invention and some of its optional aspects. The invention may be further understood by the description of the preferred embodiments, in conjunction with the drawings, which now follow.

BRIEF DESCRIPTION OF THE DRAWINGS

In the accompanying drawings,

FIG. 1 is perspective view of the combination of the reaction tube for use in performing the Polymerase Chain Reaction (PCR) in a thermal cycler and the solid plug which is nested therewithin;

FIG. 2 is a side elevational view of the combination of the reaction tube for use in performing the Polymerase Chain Reaction (PCR) in a thermal cycler and the solid plug which is nested therewithin;

FIG. 3 is a top plan view of the combination of the reaction tube for use in performing the Polymerase Chain Reaction (PCR) in a thermal cycler and the solid plug which is nested therewithin; and FIG. 4 is a central longitudinal cross-section of the combination of the reaction tube for use in performing the Polymerase Chain Reaction (PCR) in a thermal cycler and the solid plug which is nested therewithin.

DESCRIPTION OF PREFERRED EMBODIMENTS

Description of FIG. 1, FIG. 2 and FIG. 3

As seen in FIG. 1, FIG. 2 and FIG. 3, the reaction tube for use in performing the Polymerase Chain Reaction (PCR) in a thermal cycler, indicated by general numeral 10, which is the subject of the present invention includes a reaction tube 20 which consists of a lower frustoconical portion 22 terminating in a flat bottom 24, a cylindrical upper portion 26 and an upper oval lip 28. The reaction tube for use in performing the Polymerase Chain Reaction (PCR) in a thermal cycler, which is indicated by general numeral 10, is shown sealed by a cap 40 which includes a flat upper end 42.

Description of FIG. 4

As seen in FIG. 4, the reaction tube for use in performing the Polymerase Chain Reaction (PCR) in a thermal cycler, which is indicated by general numeral 10, which is the subject of the present invention includes a reaction tube 20 which, as previously described, consists of a lower frustoconical portion 22 terminating in a flat bottom 24, a cylindrical upper portion 26 and an upper oval lip 28. Reaction tube 20 is formed of a heat conducting material e.g. thin-walled polypropylene.

The cap 40 which includes a flat upper end 42 is solid and is formed of a heat insulative material.

The cap 40 includes an upper cylindrical portion 44 of the greatest diameter, a mid-portion 46 of intermediate diameter and a lower portion 48 of the least diameter. The transition 50 between upper cylindrical portion 44 of the greatest diameter and mid-portion 46 of intermediate diameter rests on the upper face 30 of the oval upper lip 28. The transition 52 between mid-portion 46 of intermediate diameter and lower portion 48 of the least diameter rests on the inner surface ledge 32 at the transition between lower frustoconical portion 22 and cylindrical upper portion 26 of reaction tube 20. As seen, when cap 40 is nested within reaction tube 20, a void space 36 is provided at the bottom of tube 20.

CONCLUSION

In summary the present invention has many advantages. Among the advantages are:

(1) The flat optically-clear bottom enables better optical detection by minimizing light reflections and refractions this minimizes internal light reflections and refractions and improves the signal-to-noise ratio.

(2) The tube has a 5 degree draft angle on the sides which is optimized for a balance between ease of ejection and thinness of tube wall.

(3) Tube lip enables tube to be ejected from the PCR instrument.

(4) The reaction tube may be loaded directly with a pipette tip.

(5) The cap is relatively easy to insert into the reaction tube, but is relatively difficult to remove.

(6) The reaction tube includes a convenient adaptor for loading.

(7) The invention provides an evaporation resistant design which has 9.25 mm thin walls and an optically-clear bottom region.

The foregoing has constituted a description of specific embodiments showing how the invention may be applied and put into use. These embodiments are only exemplary. The invention in its broadest and more specific aspects is further described and defined in the claims which follow. These claims, and the language used therein are to be understood in terms of the variants of the invention which have been described. They are not to be restricted to such variants, but are to be read as covering the full scope of the invention as is implicit within the invention and the disclosure that has been provided herein.

The invention claimed is:

1. A reaction tube comprising:
   a hollow tube of heat conducting synthetic plastic material comprising:
   a) an open top;
   b) an upper cylindrical portion;
   c) a lower frustoconical portion; and
   d) a flat bottom formed of an optically-clear material; and
   a solid plug cap, wherein the solid plug cap sealingly nests within the upper cylindrical portion and partially within the lower frustoconical portion of the hollow tube.

2. The reaction tube of claim 1, wherein the hollow tube further comprises an upper lip on the upper cylindrical portion of the hollow tube.

3. The reaction tube of claim 2, wherein the upper lip is oval in plane view.

4. The reaction tube of claim 2, wherein the solid plug cap comprises an upper cylindrical plug region and a lower cylindrical plug region.

5. The reaction tube of claim 4, wherein the solid plug cap further comprises a middle cylindrical plug region located between the upper and lower cylindrical plug regions.

6. The reaction tube of claim 5, wherein the upper cylindrical plug region is of a greater diameter than the middle cylindrical plug region.

7. The reaction tube of claim 6, wherein the middle cylindrical plug region nests within the upper cylindrical portion of the hollow tube and the lower cylindrical plug region nests within the lower frustoconical portion of the hollow tube.

8. The reaction tube of claim 7, wherein the upper cylindrical plug region rests upon the upper lip of the hollow tube.

9. The reaction tube of claim 6, wherein the hollow tube has a diameter smaller than the diameter of the upper cylindrical plug region.

10. The reaction tube of claim 5, wherein the upper cylindrical plug region is of a greater diameter than the middle cylindrical plug region and the middle cylindrical plug region is of a greater diameter than the lower cylindrical plug region.

11. The reaction tube of claim 10, wherein the middle cylindrical plug region nests within the upper cylindrical portion of the hollow tube and the lower cylindrical plug region nests within the lower frustoconical portion of the hollow tube.

12. The reaction tube of claim 1, wherein the lower frustoconical portion of the hollow tube has a draft angle of about 5 degrees.

* * * * *